United States Patent
Hsieh et al.

(10) Patent No.: US 8,280,749 B2
(45) Date of Patent: Oct. 2, 2012

(54) 12-LEAD ECG MEASUREMENT AND REPORT EDITING SYSTEM

(75) Inventors: Jui-Chien Hsieh, Taoyaun (TW);
Kuo-Chiang Yu, Taoyaun (TW);
Hsiu-Chiung Lo, Taoyaun (TW);
Chia-Chang Hung, Taoyaun (TW)

(73) Assignee: Yuan Ze University, Taoyaun (TW)

( * ) Notice: Subject to any disclaimer, the term of this patent is extended or adjusted under 35 U.S.C. 154(b) by 272 days.

(21) Appl. No.: 12/647,268

(22) Filed: Dec. 24, 2009

(65) Prior Publication Data

US 2010/0324935 A1 Dec. 23, 2010

(30) Foreign Application Priority Data

Jun. 23, 2009 (TW) .............................. 98120946 A

(51) Int. Cl.
*G06Q 10/00* (2012.01)
(52) U.S. Cl. ............ 705/2; 600/508; 600/509; 600/515; 715/738
(58) Field of Classification Search .................. 600/508, 600/509, 515; 705/2; 715/738
See application file for complete search history.

(56) References Cited

U.S. PATENT DOCUMENTS

| | | | |
|---|---|---|---|
| 2003/0229289 A1* | 12/2003 | Mohler et al. | 600/508 |
| 2006/0217623 A1* | 9/2006 | Morganroth | 600/509 |
| 2008/0262366 A1* | 10/2008 | Hunt | 600/516 |
| 2010/0058191 A1* | 3/2010 | Hawkins | 715/738 |
| 2010/0138231 A1* | 6/2010 | Linthicum et al. | 705/2 |

FOREIGN PATENT DOCUMENTS

| | | |
|---|---|---|
| TW | I251155 | 3/2006 |
| TW | 200615792 | 5/2006 |
| TW | M349516 | 1/2009 |

* cited by examiner

*Primary Examiner* — Valerie Lubin
(74) *Attorney, Agent, or Firm* — WPAT, P.C.; Anthony King

(57) ABSTRACT

The present invention provides a real-time interactive information system for measurement of 12-lead electrocardiogram waveforms and report editing, comprising a server providing cross-platform web page browsing for user to input commands or to review ECG reports and to edit or to measure information from patient further, a device for supporting internet interacting protocol which is a WEB SERVICE allowing for receiving commands issued by the server of cross-platform web page browsing and giving the server the feedback of processed ECG information by assistance from the database device, and a database device allowing for accessing patient's information to the internet interacting protocol.

13 Claims, 3 Drawing Sheets

12-LEAD ECG MEASUREMENT AND REPORT EDITING SYSTEM

FIELD OF THE INVENTION

The present invention relates to a real-time interactive information system for measurement of 12-lead electrocardiogram waveforms and report editing.

DESCRIPTION OF PRIOR ART

The conventional method to browse clinical 12-lead electrocardiogram (12-lead ECG hereafter) is via user's self-developing browsing interface or web development language, e.g. HTML or ASP.net, to read 12-lead ECG reports as described in Taiwan Patent No. M349516 and I251155 and Official Patent Gazette of Taiwan No. 200615792. Browsing only and without interaction with users is one of the disadvantages for using self-developing browsers. Common disadvantages for lacking of human-computer interaction are as follows.
1. Current electronization of ECG is only to display the paper output of the ECG report on the computer screen electronically and complete the archive management of electronic files.
2. Clinical physicians are still required to manually interpret the change of ECG waveforms, such as a height, width and slope of a waveform in a specific segment in order to provide a basis for diagnosis. However, occurrence of errors during the manual interpretation and the efficiency also should be improved. Even extracting waveforms by artificial intelligence completely is still unable to be applied to clinical practices.

SUMMARY OF THE INVENTION

The present invention relates to a real-time interactive information system for measurement of 12-lead ECG waveforms and report editing, comprising:
(a) a server providing cross-platform web page browsing for user to input commands or to review ECG reports and to edit or to measure information from patient further;
(b) a device for supporting internet interacting protocol which is a WEB SERVICE allowing for receiving commands issued by the server of cross-platform web page browsing and giving the server the feedback of processed ECG information by assistance from the database device; and
(c) a database device allowing for accessing patient's information to the internet interacting protocol.

DETAILED DESCRIPTION OF THE INVENTION

Figure 1:
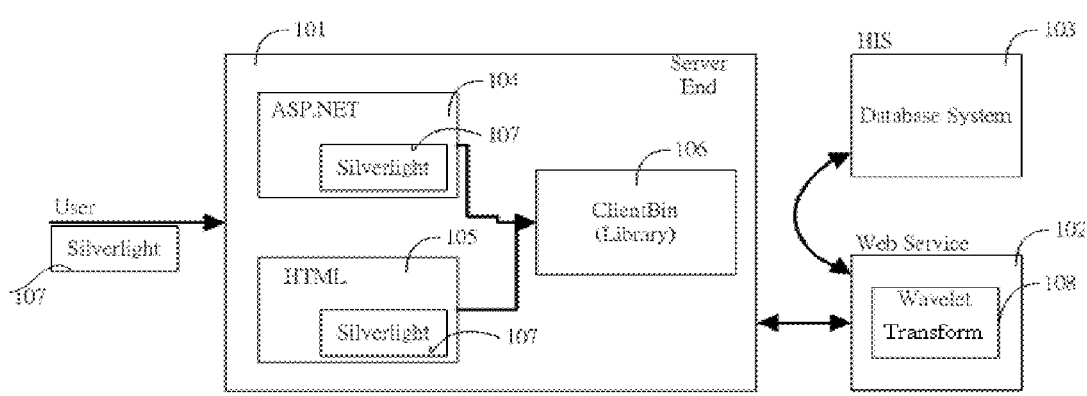
FIG. 1 illustrates a block diagram of a system architecture according to the present invention.

SILVERLIGHT, a new generation of the WEB presentation layer technology with superior vector animation and drawing ability, is designed not only to increase user experience and achieve better visual effects but also to improve the disadvantages as mentioned previously. Compared to the conventional method to which using other systems to type ECG report is required, the present invention allows medical staff to note on the report directly via interactive ECG report by SILVERLIGHT technology rather than writes comments on the paper. With paralleled display of graphs and texts, medical staff can navigate the system more intuitively without switching the window for displaying original peak signals to result-inputting one. The ECG waveform is vector-based graphic drawing, which means no distortion when the ECG report is zoomed in/out. The characteristics are as follows:
1. An ECG file editor which integrates ECG diagram, physician's opinions and treatment strategies is designed to browse ECG on the web, measure parameters of the ECG, write comments, professional opinion regarding treatment regime.
2. For the application to the patient referral, most used formats of ECG reports in Taiwan such as Philips XML-ECG and HPSCP-ECG can both be transformed to SILVERLIGHT-ECG which contains sufficient information including patient's symptoms and previously opinions to serve as reference to assist the referral process.

The present invention provides a real-time, interactive information system for measurement of 12-lead ECG waveforms and report editing. The system comprises a server providing cross-platform web page browsing for a user to input commands or to review ECG reports and to edit or to measure information from patient further, a device for supporting internet interacting protocol which is a WEB SERVICE allowing for receiving commands issued by the server of cross-platform web page browsing and giving the server the feedback of processed ECG information by assistance from the database device, and a device for providing database which is a hospital information system (HIS) facilitating logging in, inquiring, browsing or editing patient's information by using computers in or outside hospital at any time by providing the device for accessing the patient's information to the internet interacting protocol, wherein editing patient's information is to allow users for editing opinions onto the ECG reports in real-time.

The cross-platform web page browsing server of the present invention is the server with SILVERLIGHT web tech. The server comprises a device of a hypertext markup language (HTML) suite to process web page creation and performance of information on the web browser, a device of a dynamic language suite which refers to ASP.NET suite used for improving the function and convenience of dynamic web page processing, and a library system to provide functions required for server computing. The library refers to CLIENT-BIN, which can compute the waveform height and the time period width or perform message accessing and editing through assistance of a dynamic vernier with customized scale.

The cross-platform web page browsing server of the present invention is the server with SILVERLIGHT web tech. The server comprises a device of a hypertext markup language (HTML) suite to process web page creation and performance of information on the web browser, a device of a dynamic language suite which refers to ASP.NET suite used for improving the function and convenience of dynamic web page processing, and a library system to provide functions required for server computing. The library refers to CLIENT-BIN, which can compute the waveform height and the time period width or perform message accessing and editing through assistance of a dynamic vernier with customized scale.

The application of the database device comprises outpatient appointment or emergency on-site registration, price calculation of physician order, accessing and printing medication bags and medical charts, bed management, control of length of stay, price calculation from nursing station, hospital billing or submission of outpatient visit and hospitalization.

In addition, the device for internet interacting protocol of the present invention comprises a device for wavelet transform used for removing noise from ECG signal. The operational steps comprise:

(a) reception of the command from the server and a request of patient's information toward the database device;
(b) output of patient's information of ECG report and then transformation into an XML file; and
(c) collection of ECG report information to feedback to the server after removal of noise from ECG signal.

The users of the present invention are health care professional who provides service for patients, e.g. a physician, a nurse, a pharmacist, a medical technologist or a radiologic technologist.

EXAMPLES

The examples below are non-limiting and are merely representative of various aspects and features of the present invention.

Referring to FIG. 1 was the architecture diagram of system 10 of the present invention which was a real-time interactive information system for measurement of 12-lead electrocardiogram waveforms and report editing. First, the health care professional used interface of SILVERLIGHT 107 of web browser to connect to the ASP.NET website 104 and HTML website 105 in the server 101 and through log-in SILVERLIGHT 107 to inquire ECG report. Next, CLIENTBIN called WEB SERVICE 102 provided by system in pre-compiled SILVERLIGHT CLIENTBIN 106 library. Noise signal of original ECG was removed through wavelet transform 108 technology encompassed by WEB SERVICE 102. Data exchange and management with HIS database 103 was also conducted by WEB SERVICE 102 simultaneously.

Figure 2:
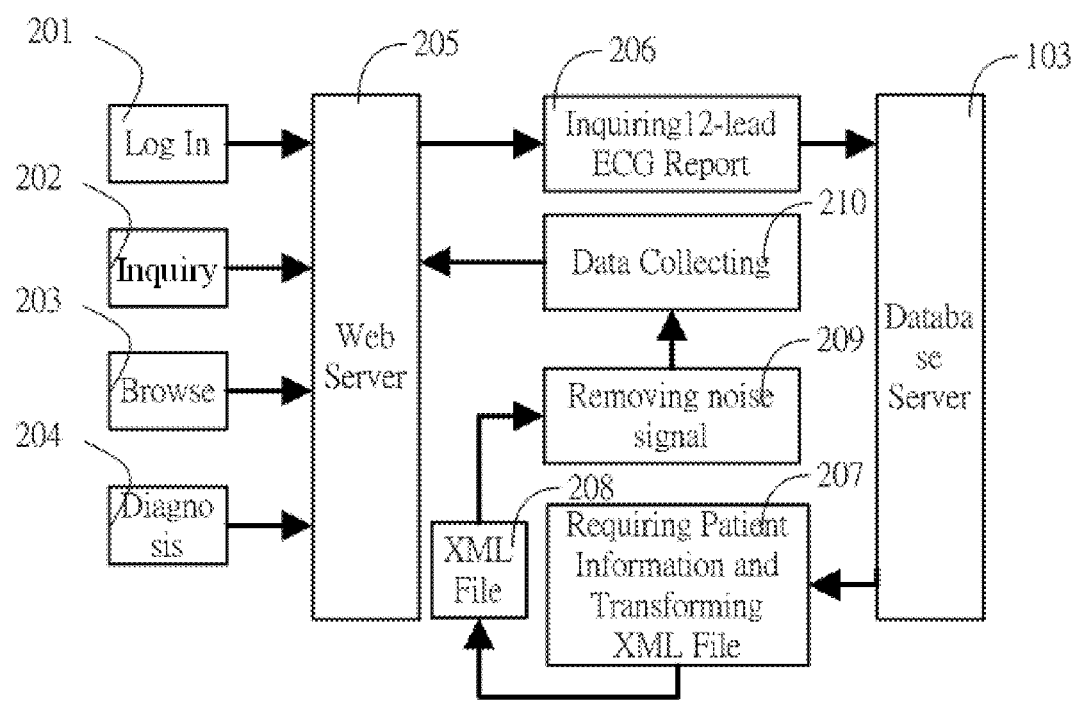
FIG. 2 illustrates a workflow diagram of a system function according to the present invention.

Referring to FIG. 2 was the function workflow diagram of the system 10. A health care professional logged in 201 web server 205 first to inquire 202 and to browse 203 12-lead ECG report 206 of a patient. After HIS database 103 received inquiry requirement, patient's information and transformed XML file 207 of the ECG report was produced. The ECG report derived from data collection 210 of XML file 208 followed by removal of noise signal 209 was feedback to web server 205 and then was displayed on user end. A health care professional was able to amplify a selected ECG signal on the picture to enable them clearly recognize signal segments which were hard to interpret manually. The health care professional was also able to change any opinion immediately on the ECG report through the function of diagnostic data editing 204 provided by the present invention.

Figure 3:
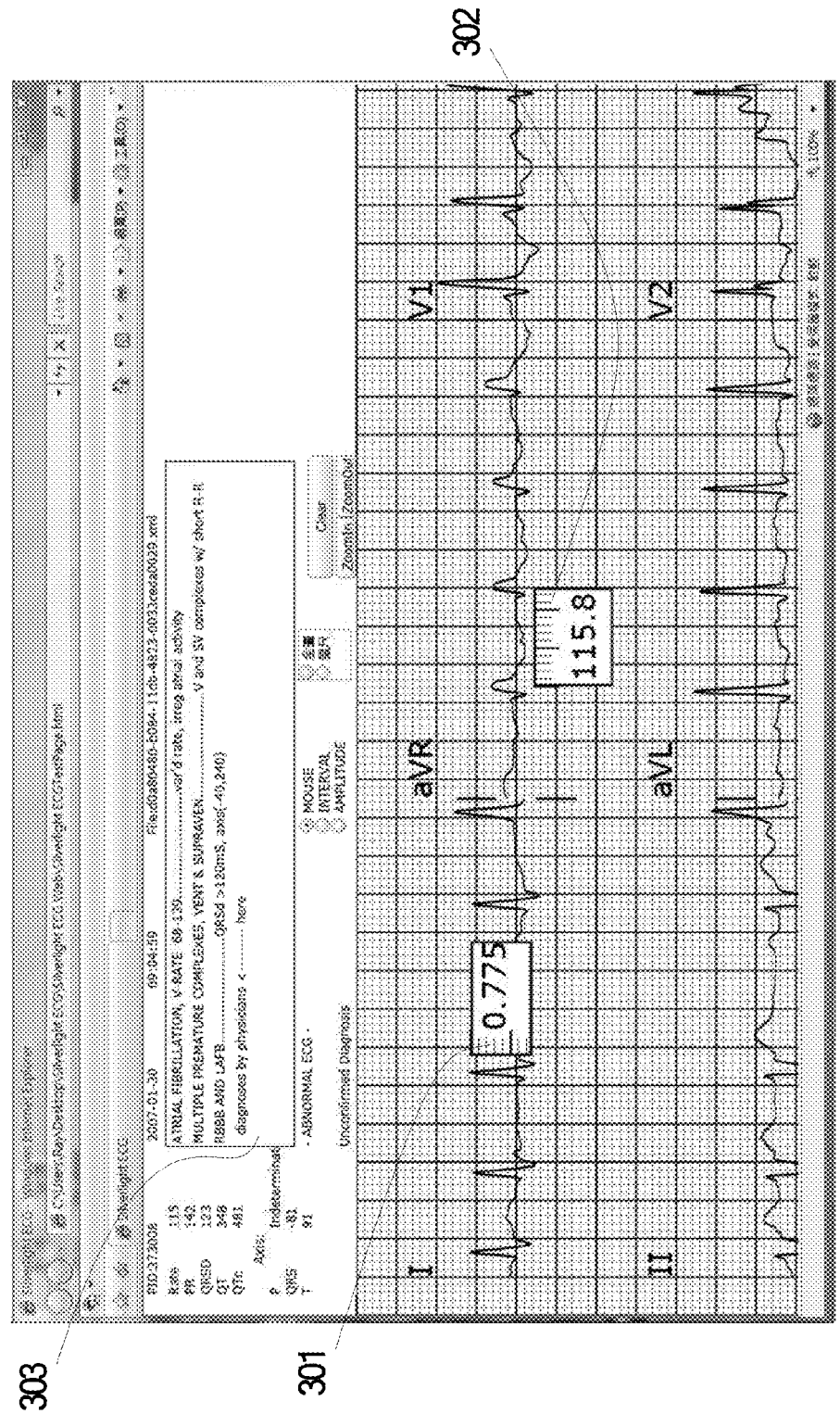
FIG. 3 illustrates waveform measurement and information editing according to the present invention.

Referring to FIG. 3 was the waveform measurement and data editing diagram of the present invention. For browsing the ECG report by the interactive ECG management system, the grids required for computing ECG grids and waveforms manually on the ECG were also improved. Furthermore, the characteristic of dynamic vernier of waveform height 301 and time period 302 was able to be presented by mouse clicking so that report modification 303 directly on the system is more convenient.

What is claimed is:

1. A real-time interactive information system for measurement of 12-lead electrocardiogram (ECG) waveforms and report editing comprising:

(a) a server providing cross-platform web page browsing for a user to input commands or to review ECG reports and to edit or to measure information from patient further;
(b) a device for supporting internet interacting protocol allowing for receiving commands issued by the server of cross-platform web page browsing and giving the server the feedback of processed ECG information by assistance from a database device;
(c) the database device allowing for accessing patient's information to the internet interacting protocol, wherein a patient's information of the ECG reports is transformed into an XML file which comprises the ECG information and noise is removed from a ECG signal in the XML file; and wherein the server providing cross-platform web page browsing further comprises a function storing means of CLIENTBIN, providing function of computing a waveform height and a time period width or performing message accessing and editing through assistance of a dynamic vernier with customized scale.

2. The system of claim 1, wherein the server providing cross-platform web page browsing comprises:
(a) a device of a hypertext markup language (HTML) suite to process web page creation and performance of information on the web browser; and
(b) a device of a dynamic language suite used for improving the function and convenience of dynamic web page processing.

3. The system of claim 1, wherein the server providing cross-platform web page browsing is a server providing technical effects from SILVERLIGHT web.

4. The system of claim 1, wherein the device for supporting internet interacting protocol uses a communication method of software from WEB SERVICE.

5. The system of claim 1, wherein the patient's information in the database device is accessed from hospital information system (HIS).

6. The system of claim 1, wherein an application of the database device comprises outpatient appointment or emergency on-site registration, price calculation of physician order, accessing and printing medication bags and medical charts, bed management, control of length of stay, price calculation from nursing station, hospital billing or submission of outpatient visit and hospitalization.

7. The system of claim 2, wherein the dynamic language suite is ASP.NET suite.

8. The system of claim 1, wherein the device for supporting internet interacting protocol further comprises a device of wavelet transform used for removing noise from ECG signal.

9. The system of claim 1, wherein the user is health care professionals who provide service for patients.

10. The system of claim 9, wherein the health care professional is a physician, a nurse, a pharmacist, a medical technologist or a radiologic technologist.

11. The system of claim 5, wherein the HIS facilitates logging in, inquiring, browsing or editing patient's information by computers in or outside hospital at any time.

12. The system of claim 1, wherein the device for supporting internet interacting protocol is configured to:
(a) receive a command from the server for a request of patient's information toward the database device;
(b) output of the patient's information of the ECG reports and then transform the information into the XML file; and
(c) collect of an ECG report information to feedback to the server after removal of noise from the ECG signal.

13. The system of claim 11, wherein the HIS facilitates editing patient's information, wherein the editing patient's information is to allow users for editing opinions onto the ECG reports in real-time.

* * * * *